United States Patent
Shi et al.

(10) Patent No.: US 6,302,845 B2
(45) Date of Patent: *Oct. 16, 2001

(54) METHOD AND SYSTEM FOR PRESSURE ESTIMATION USING SUBHARMONIC SIGNALS FROM MICROBUBBLE-BASED ULTRASOUND CONTRAST AGENTS

(75) Inventors: William Tao Shi, Haddonfield, NJ (US); Flemming Forsberg, Philadelphia, PA (US); Barry B. Goldberg, Conshohocken, PA (US); Joel S. Raichlen, Bryn Mawr, PA (US)

(73) Assignee: Thomas Jefferson University, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/272,764

(22) Filed: Mar. 19, 1999

Related U.S. Application Data

(60) Provisional application No. 60/078,823, filed on Mar. 20, 1998.

(51) Int. Cl.[7] .................................................. A61B 8/00
(52) U.S. Cl. ........................................ 600/438; 600/458
(58) Field of Search ................................. 600/437, 438, 600/458; 424/9.52

(56) References Cited

U.S. PATENT DOCUMENTS

| | | | | |
|---|---|---|---|---|
| 3,640,271 | * | 2/1972 | Horton | 600/438 |
| 4,265,251 | * | 5/1981 | Tickner | 600/438 |
| 4,483,345 | * | 11/1984 | Milwa | 600/438 |
| 5,195,520 | * | 3/1993 | Schlief et al. | 600/438 |
| 5,352,436 | * | 10/1994 | Wheatley et al. | 424/9 |
| 5,535,747 | * | 7/1996 | Katakura | 600/454 |
| 5,560,364 | | 10/1996 | Porter . | |
| 5,749,364 | * | 5/1998 | Sliwa, Jr. et al. | 600/458 |

OTHER PUBLICATIONS

Chang, P.H., Shung K.K. and Levene, H.B., 1996. Quantitative measurements of second harmonic Doppler using ultrasound contrast agents. *Ultrasound Med Biol* 22, pp. 1205–1214.

Forsberg, F., Goldberg, B.B., Liu, J.B., Merton, D.A. and Rawool, N.M., 1996. On the feasibilty of real–time, in vivo harmonic imaging with proteinaceous microspheres. *J Ultrasound Med* 15, pp. 853–860.

Goldberg, B.B.., Liu, J.B. and Forberg, F., 1994. Ultrasound contrast agents: a review. *Ultrasound Med Biol* 20, pp. 319–333.

Gramiak, R. and Shah, P.M., 1968. Echocardiography of the aortic root. *Invest Radiol* 3, pp. 356–366.

(List continued on next page.)

*Primary Examiner*—Francis J. Jaworski
(74) *Attorney, Agent, or Firm*—Clifford Kent Weber, Esq.

(57) ABSTRACT

The present invention relates to the use of diagnostic ultrasound and microbubble-based ultrasound contrast agents to accomplish noninvasive subharmonic aided pressure estimation (SHAPE) in the cavity of the heart, in other organs, and in major blood vessels. Diagnostic ultrasound provides noninvasive, real-time cross-sectional images and parameter estimations without ionizing radiation and without the disadvantages and risks of invasive methods of imaging and measurement. SHAPE is a non-invasive, direct, and accurate method for pressure estimation utilizing sub-harmonic or ultraharmonic signals from contrast agents. In light of the advantages of diagnostic ultrasound, SHAPE provides an economical alternative, a safe avenue, and an earlier timetable for assessing the clinical condition of patients, especially critically ill patients.

5 Claims, 15 Drawing Sheets

OTHER PUBLICATIONS

Krishna, P.D. and Newhouse, V.L., 1997. Second harmonic characteristics of the ultrasound contrast agents Albunex and FS069. *Ultrasound Med Biol* 23, pp. 453–459.

Ophir, J. and Parker, K.J., 1989. Contrast agents in daignostic ultrasound. *Ultrasound Med Biol* 15, pp. 319–325.

Schrope, B.A. and Newhouse, V.L., 1993. Second harmonic ultrasound blood perfusion measurement. *Ultrasound Med Biol* 19, pp. 567–579.

van Liew, H.D. and Burkard, M.E., 1995. Bubbles in circulating blood: Stablization and simulations of cyclic changes of size and content. *J Appl Physiol* 79, pp. 1379–1385.

Wu, J. and Tong, J., 1998. Experimental study of stability of a contrast agent in an ultrasound field. *Ultrasound Med Biol* 24, pp. 257–265.

* cited by examiner

METHOD AND SYSTEM FOR PRESSURE ESTIMATION USING SUBHARMONIC SIGNALS FROM MICROBUBBLE-BASED ULTRASOUND CONTRAST AGENTS

This application claims the benefit of Provisional application Ser. No. 06/078,823, filed Mar. 20, 1998.

FIELD OF THE INVENTION

The present invention generally relates to the field of ultrasound imaging and methods of utilizing ultrasound contrast agents containing microbubbles, and more particularly to the use of such ultrasound contrast agents to accomplish noninvasive sub-harmonic aided pressure estimation inside the human body, especially in the cavities of the heart and in major vessels (e.g., the portal vein).

BACKGROUND OF THE INVENTION

Diagnostic ultrasound has become a very successful modality in clinical radiology because ultrasound imaging and measurement can provide noninvasive, real-time cross-sectional images and parameter estimations of soft tissue structures and blood flow without ionizing radiation. The advantages of noninvasive methods of imaging and measurement over invasive methods of imaging and measurement include the following: 1) the patient is not subjected to a general procedure involving penetrating the body nor is the patient subjected to the risks associated with an invasive imaging procedure, such as catherization; 2) where imaging and measurement are necessary to assess a patient's condition, noninvasive imaging and measurement are less dangerous alternatives, particularly when the patient's clinical condition is too unstable to permit an invasive procedure; 3) noninvasive imaging and measurement may better enable treating physicians and surgeons to provide an earlier and more focused method of intervention, thereby leading to a safer avenue and an earlier timetable for stabilization of critically ill patients, and 4) noninvasive imaging and measurement can significantly reduce the cost of clinical examinations.

Currently there are no methods available for direct noninvasive measurement of internal cavity pressure. Noninvasive pressure estimation in the cavities of the heart and in major vessels (e.g., the portal vein) would provide clinicians with a valuable tool for assessing patients with valvular heart disease, congestive heart failure and various vascular diseases. Measurement of cavity pressure is important in determining blood flow in the cardiovascular system. Accurate pressure estimation is a key parameter in assisting minute-to-minute settings for patients in intensive care settings. Such measurements would inform the physician of altered physiologic states caused by disease, especially where pressure has become abnormally high or abnormally low. These pressure measurements may be especially useful in emergency settings.

Some microbubble-based ultrasound contrast agents are particularly well suited for pressure measurements because their substantial compressibility enables the microbubbles to vary significantly in size in response to changes in pressure. Pressure changes in turn affect reflectivity of microbubbles after intravenous injection of a contrast agent. It is known that the diagnostic capabilities of ultrasound imaging can be improved by intravenous injection of ultrasound contrast agents (Ophir, J. and Parker, K. J. Contrast Agents in Diagnostic Ultrasound. *Ultrasound Med Biol* 15: 319–325, 1989; Goldberg, B. B., Liu, J. B. and Forsberg, F. Ultrasound Contrast Agents: A Review. *Ultrasound Med Biol* 20: 319–333, 1994). Most contrast agents consist of microbubbles of less than 10 $\mu$m in diameter in order to circulate through capillaries (Needleman, L. and Forsberg, F. Contrast Agents in Ultrasound. *Ultrasound Quarterly* 13: 121–138, 1996). Such microbubbles can significantly enhance the backscatter from blood. Moreover, the nonlinear properties of these microbubbles can be used to create new harmonic and subharmonic imaging modalities (Schrope, B. A., and Newhouse, V. L., Second Harmonic Ultrasound Blood Perfusion Measurement. *Ultrasound Med Biol* 19: 567–579, 1993; Shi, W. T., Forsberg, F. and Goldberg, B. B. Subharmonic Imaging with Gas-filled Microbubbles, *J Acoust Soc Am* 101, 3139 (abstract), 1997) for detection of blood flow in small or even capillary blood vessels surrounded by stationary or moving tissue.

Contrast microbubbles are often stabilized with a coating of surfactants or with encapsulating elastic shells. (de Jong, N., Hoff, L., Skotland, T. and Bom, N. Absorption and Scatter of Encapsulated Gas Filled Microspheres: Theoretical Considerations and Some Measurements. *Ultrasonics* 30: 95–103, 1996). The materials on the bubble surface will greatly influence the response of the contrast microbubbles to hydrostatic pressure changes. De Jong and colleagues investigated the effect of the static ambient pressure on the size change of Albunex® (Molecular Biosystems Inc., San Diego, Calif.) and Quantison™ (Andaris Ltd., Nottingham, UK) microbubbles. (de Jong, N., Ten Cate, F. J., Vletter, W. B. and Roelandt, J. R. T. C. (1993). Quantification of Transpulmonary Echocontrast Effects. Ultrasound Med Biol 19: 279–288; de Jong, N. (1996). Improvements in Ultrasound Contrast Agents. *IEEE Eng Med Biol Mag* 15: 72–82). Most of the Albunex encapsulated microbubbles shrunk and disappeared due to over-pressure, while the Quantison gas-filled microparticles were insensitive to pressure changes due to their rigid shells.

The reflectivity of microbubble contrast agents at the transmit frequency has been found to vary with the hydrostatic blood pressure. Videodensity variations measured during a cardiac cycle in both the ventricles and especially in the left ventricle indicated a large pressure dependence for microbubbles based on sonicated albumin. (Shapiro, J. S., Reisner, S. A., Lichtenberg, G. S. and Meltzer, R. S. Intravenous Contrast Echocardiography with Use of Sonicated Albumin in Humans: Systolic Disappearance of Left Ventricular Contrast after Transpulmonary Transmission. *J Am Coll Cardiol* 7: 1603–1607, 1990; de Jong et al. Quantification of Transpulmonary Echocontrast Effects. *Ultrasound Med Biol* 19: 279–288, 1993). This was further confirmed by Gottlieb et al. in an in vitro model. (Gottlieb, S., Ernst, A. and Meltzer, R. S. Effect of Pressure on Echocardio-graphic Videodensity from Sonicated Albumin: An in vitro Model. *J Ultrasound Med* 14: 101–108, 1995). The effect of hydrostatic pressure on the acoustic transmittance of an Albunex microbubble suspension was studied by Brayman et al (1996), who found that the acoustic transmittance increased with hydrostatic pressure. (Brayman, A. A., Azadniv, M., Miller, M. W. and Meltzer, R. S. Effect of Static Pressure on Acoustic Transmittance of Albunex Microbubble Suspensions. *J Acoust Soc Am* 99: 2403–2408, 1996). This effect could be caused by the destruction of many of the microbubbles at a pressure comparable to those produced in the heart. The reflectivity of some other agents such as Levovist® (Schering A G, Berlin, Germany) was reported to be less sensitive to pressure changes. (Schlief, R. Galactose-based Echo-enhancing agents in *Ultrasound Contrast Agents,* edit by Barry B. Goldberg, Martin Dunitz Ltd, London. pp 75–82, 1997).

There are many interesting bubble oscillations which span the range of possible frequency emissions from subharmonics (as well as ultraharmonics) through higher harmonics (Lauterborn, W. Numerical Investigation of Nonlinear Oscillations of Gas Bubble in Liquids. *J Acoust Soc Am* 59: 283–293, 1976). Subharmonic oscillation (or ultraharmonic oscillation) of a free bubble occurs only when the exciting acoustic signal exceeds a certain threshold level (Prosperetti, A. Nonlinear Oscillations of Gas Bubble in Liquids: Transient Solutions and the Connection between Subharmonic Signal and Cavitation, *J Acoust Soc Am* 57: 810–821, 1975; Prosperetti, A. Application of the Subharmonic Threshold to the Measurement of the Damping of Oscillating Gas Bubbles. *J Acoust Soc Am* 61: 11–16, 1977; Leighton, T. G., *The Acoustic Bubble*. Academic Press, London, Great Britain, 1994), while the generation of higher harmonics is a continuous process and occurs to various degree for all levels of excitation. Eller and Flynn estimated the threshold acoustic pressure required for subharmonic generation from a spherical bubble driven by a sinusoidal pressure field. (Eller, A. and Flynn, H. G. Generation of Subharmonics of Order One-Half by Bubble in a Sound Field. *J Acoust Soc Am* 46: 722–727, 1969). They found that the threshold pressure showed a pronounced minimum for bubbles which are close to twice the size of those resonant with the insonifying field. Neppiras (1968) experimentally studied the subharmonic emission from free gas bubbles subjected to sound field with intensities up to the transient cavitation threshold. (Neppiras, E. A. Subharmonic and Other Low-Frequency Emission from Bubbles in Sound-Irradiated Liquids. *J Acoust Soc Am* 46: 587–601, 1968). The subharmonic emission of a free gas bubble under two-frequency excitation was measured by Leighton et al (1991) and Phelps and Leighton (1996) for the determination of the bubble size. (Leighton, T. G., Lingard, R. J., Walton, A. J. and Field, J. E. Acoustic Bubble Sizing by Combination of Subharmonic Emission with Imaging Frequency. *Ultrasonics* 29; 319–323, 1991; Phelps, A. D., and Leighton, T. G. High-Resolution Bubble Sizing through Detection of the Subharmonic Response with a Two-Frequency Excitation Technique. *J Acoust Soc Am* 99: 1985–1992, 1996).

Microbubble-based agents not only produce helpful enhancement of backscattered signals but also generate significant superharmonics and subharmonics of incident ultrasound waves. The subharmonic of the order ½ and ultraharmonic of the order 3/2 were observed in the spectrum of insonated Levovist microbubbles by Schrope et al. (Schrope, B. A., Newhouse, V. L. and Uhlendorf. V. Simulated Capillary Blood Flow Measurement Using a Nonlinear Ultrasonic Contrast Agent. *Ultrasonic Imaging* 14: 134–158, 1992). Chang et al. acquired a Doppler power spectrum of the subharmonic response of Albunex microbubbles. (Chang, P. H., Shung, K. K., Wu, S. and Levene, H. B. Second Harmonic Imaging and Harmonic Doppler Measurements with Albunex," *IEEE Trans Ultrason Ferroelec Freq Contr* 42: 1020–1027, 1995). Lotsberg et al. investigated the subharmonic emission of Albunex and found no sharp threshold as expected from theory for free bubbles. (Lotsberg, O., Hovem, J. M. and Aksum, B. Experimental Observation of Subharmonic Oscillations in Infoson Bubbles. *J Acoust Soc Am* 99: 1366–1369, 1996). Shi et al. investigated the subharmonic response of a surfactant-coated microbubble agent to different transmit ultrasound pulses. (Shi, W. T., Forsberg, F., Gupta, M., Alessandro, J., Wheatley, M. A. and Goldberg, B. B. Subharmonic Response of a New US Contrast Agent. *Radiology* 205(P): 353 (abstract), 1997). Shankar et al. (1998) found that the ratio of the subharmonic signal scattered from contrast microbubbles to that from soft tissues is greater than the microbubble-to-tissue ratio of the second harmonic signals. (Shankar, P. M., Krishna, P. D. and Newhouse, V. L. Advantages of Subharmonic over Second Harmonic Backscatter for Contrast-to-tissue Echo Enhancement. *Ultrasound Med Biol* 24: 395–399, 1998).

The most important factor responsible for the use of microbubbles as contrast agents lies in the difference in compressibility between the bubble and the surrounding medium. For a bubble filled with an ideal gas (e.g., air) at atmospheric pressure, the compressibility is nearly 16,000 times greater than the compressibility of water. This allows microbubbles to change substantially in size in response to pressure changes. Changes in the size, in turn, should affect the reflectivity of microbubble contrast agents. This suggests that the intensity of scattered contrast signals may be utilized for the noninvasive detection of pressure changes. The noninvasive estimation of pressures in heart cavities and major vessels would provide clinicians with an invaluable tool for assessing patients with cardiac and vascular diseases, including valvular heart disease, congestive heart failure, portal hypertension and various other vascular diseases. Currently, only the maximum pressure difference across the valves of the heart can be measured non-invasively using Doppler ultrasound and the Bernoulli equation. (Evans, D. H., McDicken, W. N., Skidmore, R. and Woodcock, J. P. *Doppler Ultrasound: Physics, Instrumentation and Clinical Applications*. John Wiley & Sons, London, UK, 1989).

The dependence of harmonic and sub-harmonic responses on hydrostatic pressure has been studied. (Shi, W. T., Raichlen, J. S., Forsberg, F. and Goldberg, B. B. Effect of Ambient Pressure Change on Subharmonic Response of Microbubbles. *J Ultrasound Med,* S55: (abstract), 1998; Shi W T, Forsberg F, Raichlen J S, Needleman L, Goldberg B B. Pressure dependence of subharmonic signals from contrast microbubbles. *Ultrasound Med Biol* 25: 275–283, 1999). In the present invention, results with a galactose-based contrast agent indicate that, over the pressure range of 0–186 mmHg, the subharmonic amplitude of scattered signals decrease by around 10 dB under optimal acoustic settings while the first and second harmonic amplitudes decrease only an average about 2 dB. An excellent correlation (r=0.98) between the subharmonic amplitude and the hydrostatic pressure demonstrates that the subharmonic signal is an excellent indicator for noninvasive detection of pressure changes. The correlation (r=0.98) between the subharmonic amplitude and the hydrostatic pressure was obtained at the growth stage of subharmonic generation.

Based on the measurements made, a technique called SHAPE (Sub-Harmonic-Aided Pressure Estimation) is described in the present invention. SHAPE is a non-invasive, accurate, and direct technique to measure changes in pressure. This technique can be implemented in both penetration and resolution modes in a stand-alone system or in a modified commercial medical ultrasound scanner.

SHAPE allows the clinician to use a non-invasive method of obtaining pulmonary pressures, as well as pressure gradients in the heart. Likewise, SHAPE permits clinicians to follow patients with portal hypertension and associated complications (which may include death) and, therefore, permits earlier intervention to prevent serious complications. Additionally SHAPE enables clinicians to obtain the very important clinical measurement of post-stenotic pressure reductions in patients with claudication (e.g. in the head or kidneys).

In summary SHAPE is a much better approach for pressure measurement than any currently available methods of pressure measurement.

SUMMARY OF THE INVENTION

It is an object of the present invention to provide a direct noninvasive measurement of hydrostatic pressure. It is a further object of the present invention to take a new approach to noninvasive pressure estimation in the cavities of the heart and in major vessels (e.g., the portal vein) to provide clinicians with a valuable tool for assessing patients with various diseases, including but not limited to, valvular heart disease, congestive heart failure, portal hypertension, and other vascular diseases.

It is a further object of the present invention to provide new techniques to estimate internal pressure variations with a microbubble-based ultrasound contrast agent by transmitting at one frequency but receiving only at subharmonic (or ultraharmonic) frequencies with analog or digital filtering techniques. The invention can be implemented in both the resolution and penetration modes as a stand alone system or in a modified commercial ultrasound scanner.

It is another object of the present invention to provide a method of measuring pressure changes in a mammal, comprising: application of a contrast agent containing microbubbles into said mammal; an ultrasound system with analog or digital filtering for detecting said microbubbles, said ultrasound system capable of transmitting at least one ultrasound detection signal and capable of receiving ultrasound signals that are scattered by said microbubbles, wherein said ultrasound signals received by said ultrasound system include at least one of the group of subharmonic and ultraharmonic signals; and measurement of the amplitude of at least one of the group of subharmonic and ultraharmonic signals to estimate said pressure changes in said mammal.

It is another object of the present invention to provide a system for measuring pressure changes in a mammal, comprising: an ultrasound system with analog or digital filtering for detecting microbubbles, said ultrasound system capable of transmitting at least one detecting signal and capable of receiving detection signals that are scattered and returned by said microbubbles, wherein said detection signals received by said ultrasound system include at least one of the group of subharmonic and ultraharmonic signals; said ultrasound system having at least one single-element transducer for pressure estimation.

It is another object of the present invention to provide a system for measuring pressure changes in a mammal, comprising: an ultrasound system with analog or digital filtering for imaging microbubbles, said ultrasound system capable of transmitting at least one detecting signal and capable of receiving detection signals that are scattered and returned by said microbubbles, wherein said detection signals received by said ultrasound system include at least one of the group of subharmonic and ultraharmonic signals; said ultrasound system having one of the group of a phase transducer array with a capability of beam steering, a linear transducer array with at least one transducer, or a curved transducer array.

It is another object of the present invention to provide an ultrasound contrast agent used for pressure estimation with said ultrasound contrast agent containing microbubbles, wherein said microbubbles have a narrow band of size distribution and are stable when circulating within a mammal bloodstream such that size uniformity of said microbubbles is maintained during circulation and said microbubbles are substantially compressible such that said microbubbles change significantly in size in response to changes in pressure and said response of said microbubbles to changes in pressure maximizes the intensity of at least one of the group of subharmonic and ultraharmonic signals scattered from said microbubbles.

It is another object of the present invention to provide A method of using an ultrasound contrast agent containing microbubbles to estimate pressure change in a mammal, comprising: application of said microbubbles, wherein said microbubbles have a narrow band of size distribution and are substantially compressible such that said microbubbles change significantly in size in response to changes in pressure; measurement of shifts in resonance frequency of one of the group of subharmonic or ultraharmonic signals received by an ultrasound system having analog or digital filtering for detection of said microbubbles, wherein said resonance frequency shifts result from changes in the size of said microbubbles and said size changes correspond to changes in hydrostatic pressure.

DETAILED DESCRIPTION

The present invention relates to ultrasound contrast agents containing microbubbles to accomplish noninvasive subharmonic aided pressure estimation in the cavities of the heart, in other organs, and in major vessels (e.g., the portal vein). The pressure dependence of subharmonic signals from contrast microbubbles was determined with the measurement system shown in FIGS. 1 and 2.

Figure 1:
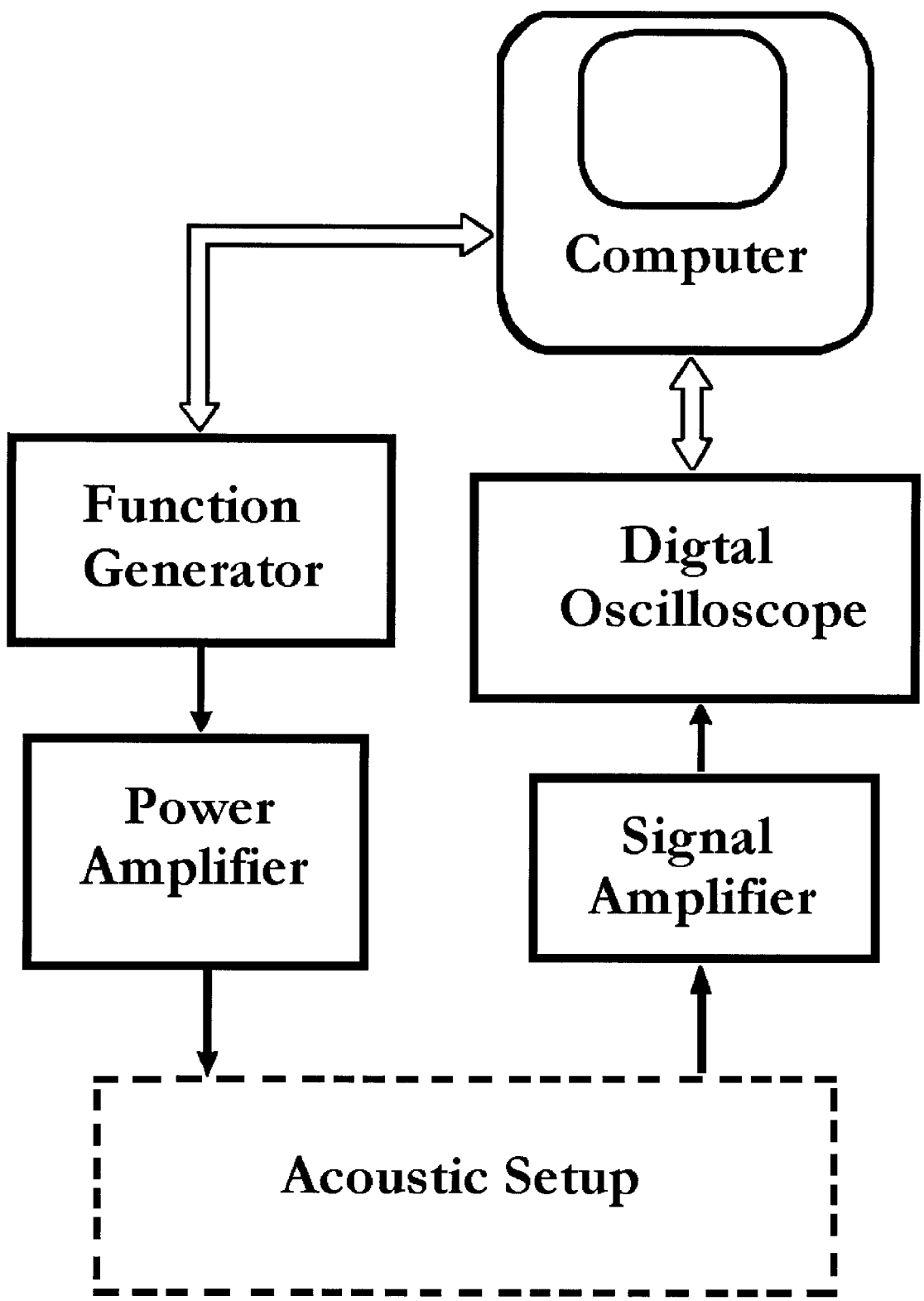
FIG. 1. Electronic part of the measurement system

The block diagram of the electronic part of the measurement system is presented in FIG. 1. A programmable function generator (Model 8116A, Hewlett Packard, Santa Clara, Calif.) produced pulses for transmission. The transmit signals were first amplified in a broadband 50 dB RF power amplifier (Model 325LA, ENI, Rochester N.Y.) and then supplied to an acoustic transmit transducer. Signals scattered from contrast microbubbles were sensed by a receive transducer and amplified with a low noise RF amplifier (Model 5052 PR, Parametrics, Waltham, Mass.). The amplified signals were then digitized using a digital oscilloscope equipped with mathematical functions (Model 9350AM, LeCroy, Chestnut Ridge, N.Y.). The digitized signals were further processed with the FFT spectrum analysis in the digital oscilloscope. The amplitude of the harmonic and subharmonic signal components were obtained from spectra averaged over 64 sequences. The command delivery to the function generator and the data transfer from the digital oscilloscope were controlled by a personal computer via LabView® (National Instruments, Austin, Tex.).

The acoustic setup for the measurement of acoustic attenuation is given in FIG. 2(a). A single-element flat transducer (Etalon Inc., Lebanon, Ind.) was used as both the ultrasound transmitter and receiver. This transducer has a diameter of 2.5 cm and a center frequency of 3.6 MHz with 98% bandwidth. A Transmit/Receive switch (Model RDX-6, Ritec Inc., Warwick, R.I.) was employed to separate transmit and receive signals. Crosstalk from the transmit signals was eliminated with a double-mixer range gate. A flat stainless steel plate was placed in the front of the transducer as an acoustic reflector. Both the transducer and the reflector were put in a container filled with 1.0 liter of water. Short pulses with a duration of 0.16 ms (6.0 MHz, 1 cycle) were sent at a PRF (Pulse Repetition Frequency) of 5 Hz. The traveling distance of the ultrasound pulses was limited to 5 cm to minimize the influence of diffraction (mostly beam expansion) owing to the limited aperture of the transducer. The acoustic attenuation of a contrast agent suspension as a function of frequency was determined by subtracting the average spectrum of received signals prior to injection of the contrast agent from the spectrum after the injection.

The subharmonic response of contrast microbubbles to different transmit pulses at atmospheric pressure was investigated using two single-element focused transducers, as shown in FIG. 2(b). A transducer with a bandwidth of 38% and a center frequency of 2.2 MHz (Staveley, East Hartford, Conn.) was used as transmitter and another transducer with a bandwidth of 86% and a center frequency of 3.6 MHz (Etalon, Lebanon, Ind.) as receiver. Both transducers have a diameter of 2.5 cm and a focal length of 5.0 cm. They were positioned confocally at the right angle to each other and place in a container filled with 1.0 liter of water. This transducer arrangement substantially enhances the spatial resolution of the acoustic measurements. Because the size of microbubbles are much smaller than the acoustic wavelength, the scattering pattern from the microbubbles will be isotropic, i.e., the waveforms of 90°-scattered signals should be very similar to those of the backscattered echoes. The acoustic output of the transmit transducer was calibrated in water using a 0.5 mm broadband acoustic hydrophone (Precision Acoustics Ltd., Dorchester, UK).

The subharmonic response at different static pressures was measured using a sealed 2.25 liter water tank that can sustain pressure changes at least 200 mmHg, as shown in FIG. 2(c). The same transducer pair as shown in FIG. 2(b) was employed. The two transducers are positioned at an angle of about 60° to each other. A thin plastic acoustic window was constructed on the wall of the tank for acoustic transmission. The tank was immersed in a water bath where temperature can be controlled. The pressure inside the tank was monitored by a pressure gauge (OMEGA Engineering Inc., Stamford, Conn.). An inlet and an outlet on the tank were constructed for injecting microbubble suspensions and applying extra hydrostatic pressures.

All measurements were carried out with injection of a suspension of specially made Levovist (Batch 61139 for in-vitro use only) into water at room temperature (around 25° C.). Levovist is a galactose-based contrast agent with 98% of all microbubbles less than 10 $\mu$m in diameter. The Levovist suspension is made by adding 12 ml distilled water into one vial of 2.5 gram Levovist granules, shaking it vigorously for about 10 seconds, and leave it to stand for about 2 minutes. Water is utilized as the carrying and propagation medium. The water in the containers was kept in circulation by a magnetic stirrer.

The resonance response of Levovist microbubble suspensions were investigated since the subharmonic emission depends on the resonance of contrast microbubbles. According to free bubble theory, a bubble is a much better scatterer with relatively strong subharmonic emission when the bubble is insonified at its resonance frequency. The resonance response of a contrast agent is related to both the size distribution of the microbubbles and the resonance response of each individual microbubbles. A simple way to quantify the resonant response of a contrast agent is to determine its acoustic attenuation as a function of frequency (de Jong et al. Absorption and Scatter of Encapsulated Gas Filled Microspheres: Theoretical Considerations and Some Measurements. *Ultrasonics* 30: 95–103, 1992; Cachard, C., Bouakkaz, A. and Gimenez, G. In Vitro Evaluation of Acoustic Properties of Ultrasound Contrast Agents: Experimental Set-up and Signal Processing. *Ultrasonics* 34: 595–598, 1996). Acoustic attenuation of each Levovist microbubble suspension was measured using the acoustic arrangement shown in FIG. 2(a). It was observed that the attenuation increased by approximately a factor of two when the injection dose was doubled. The resonance response of a Levovist suspension with a concentration of 0.31 gram Levovist granules per a liter of water (gram/liter) is given in FIG. 3. The measurements were carried out with an injection of 1.5 ml Levovist suspension into 1.0 liter water. FIG. 3 shows a good resonance response for Levovist in the frequency range from 1.0 to 5.0 MHz with the peak resonance frequency of around 3.0 MHz.

The harmonic and subharmonic responses of Levovist microbubbles to ultrasound pulses at atmospheric pressure were investigated with the acoustic arrangement shown in FIG. 2(b). The experimental design has the advantage that scattered signals only come from the microbubbles in the small confocal region of the transmit and receive transducers. Therefore the influence of axial acoustic pressure distribution on acoustic pulses of different lengths is minimized. The ultrasound pluses were transmitted at a center frequency of 2.0 MHz because of both strong resonance response and the fast increase in resonance response with frequency at 2 MHz. It is expected that the first harmonic response at 2 MHz will decrease as the ambient pressure is raised. The curve of the resonance response in FIG. 3 will be shifted to the right side in response to overall size reduction of the microbubbles due to the increase in hydrostatic pressure.

Figure 4:
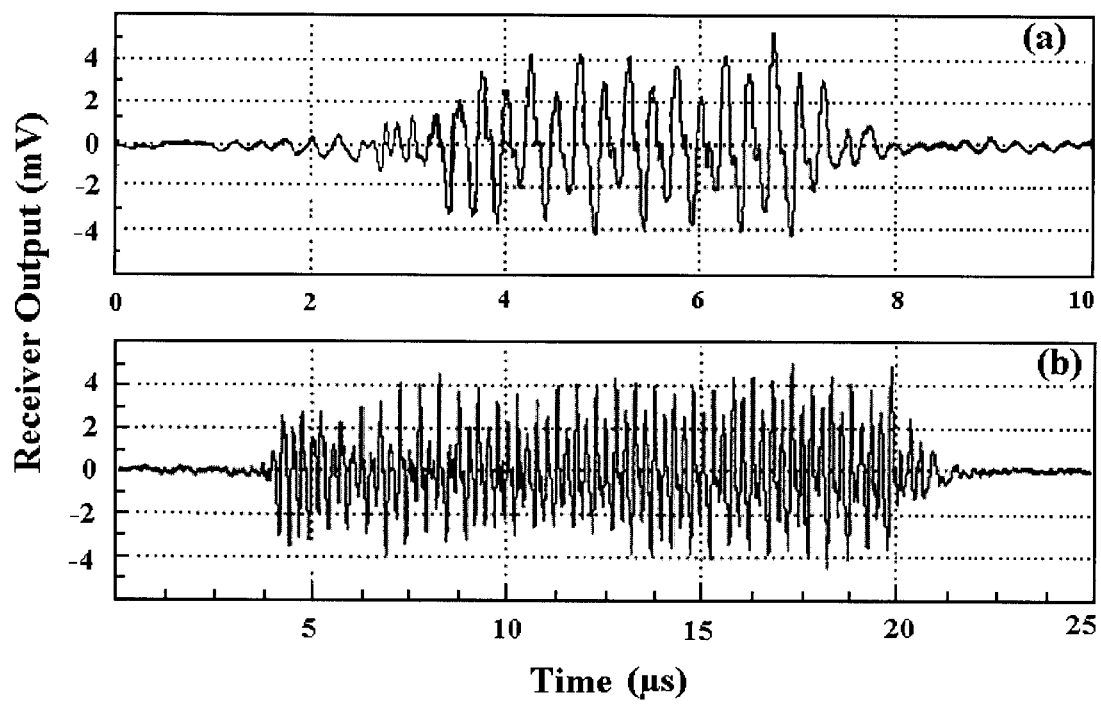
FIG. 4. Time histories and spectra of scattered signals

Time histories of scattered signals for 16-cycle and 64-cycle transmit ultrasound pulses were recorded, as shown in FIGS. 4(a) and 4(b), respectively, for a concentration of 0.083 gram/liter. The response of the contrast microbubbles took around 3 acoustic cycles to grow to their full oscillation amplitudes. This indicates that short transmit pulses with 2–4 cycles in length can be utilized to generate sufficient subharmonic signals. The strong subharmonic response to transmit pulse of 4–32 cycles was found for ST68 contrast microbubbles (Shi et al. Subharmonic Response of a New US Contrast Agent. *Radiology* 205(P): 353 (abstract), 1997). ST68 is an experimental agent produced by Dr. Wheatley and her colleagues at Drexel university. (Wheatley, M. A., Peng, S., Singhal, S. and Goldberg, B. B. (1993). Surfactant-stabilized Microbubble Mixtures, Process for Preparing and methods of Using the Same. U.S. Pat. No. 5,352,436). In both FIGS. 4(a) and (b), the subharmonic modulation at every two transmit acoustic periods is observed with high and low peaks interlacing. The corresponding spectra are given in FIGS. 4(c) and 4(d), respectively. Significant discrete subharmonic components of the order ½ can be seen for both 16-cycle and 64-cycle transmit pulse. This indicates that both short and long pulses may be utilized to generate sufficient subharmonic signals. In the following experiments, 64-cycle transmit pulses were employed. The use of long transmit pulses not only enhanced signal-to-noise ratio for the subharmonic components in received scattered signals, but also helped reduce the transient effect of the pulse length on the harmonic and subharmonic responses.

Figure 5:
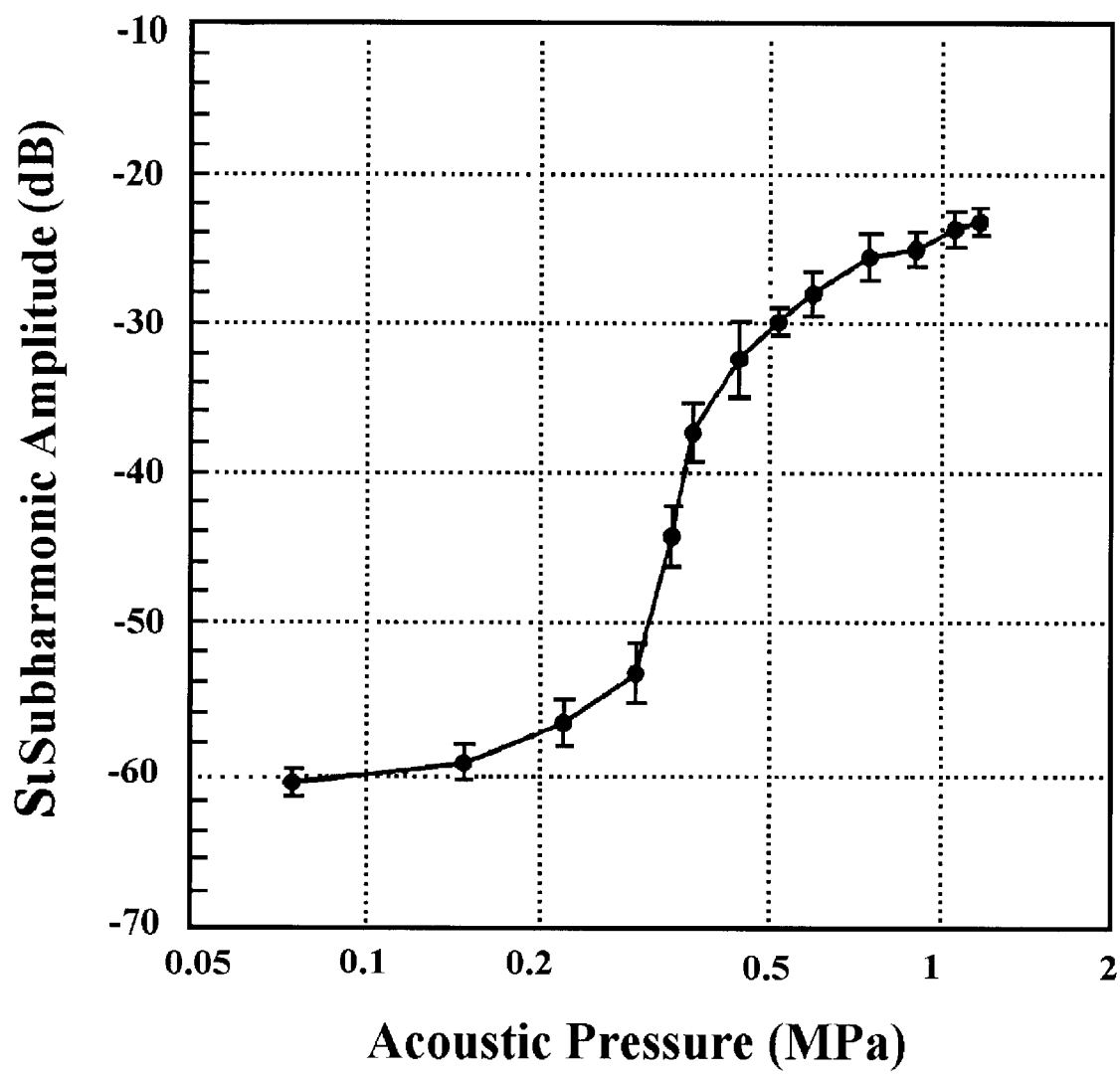
FIG. 5. Subharmonic response of Levovist

The amplitude of the subharmonic component as a function of incident acoustic pressure is plotted in FIG. 5. The experiments were conducted using Levovist suspensions with a concentration of 0.10 gram/liter. The first and second harmonic components were found to increase gradually with the acoustic pressure although the second harmonic component increases at a greater rate. In FIG. 5, the subharmonic component acts quite different with a rapid growth in the intermediate acoustic pressure range of around 0.3–0.6 MPa. The subharmonic component increase with acoustic pressure at much slower rates at both lower and higher acoustic pressures. Standard deviations in the measurements were mainly caused by the decay of microbubble reflectivity with time.

Figure 6A:
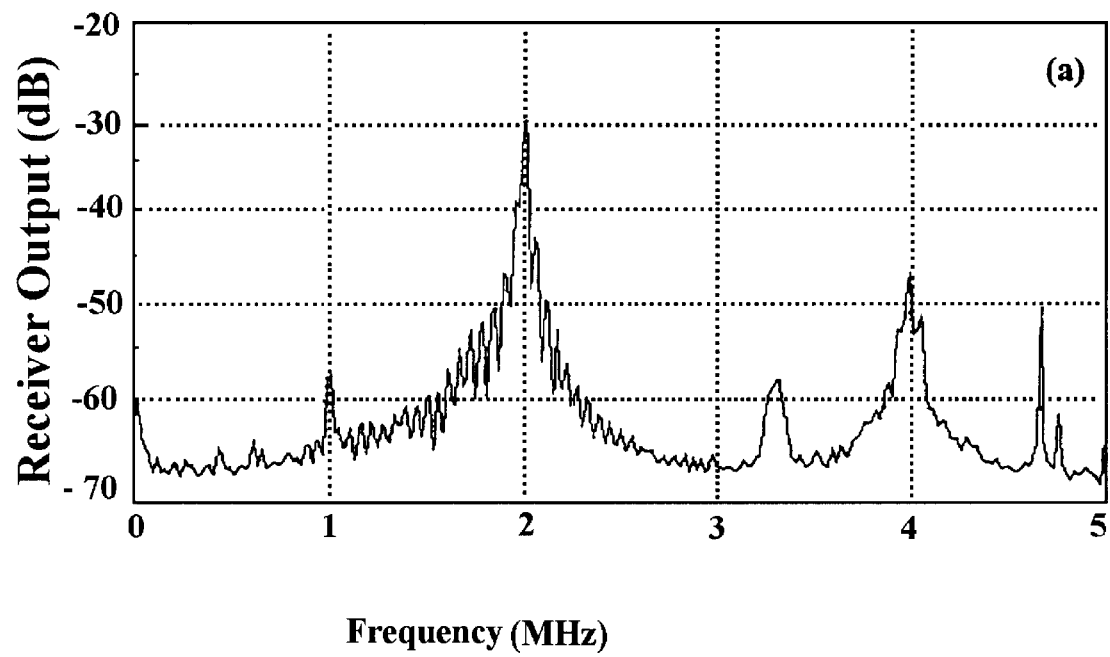
FIG. 6. Spectra at different acoustic pressures
Figure 6B:
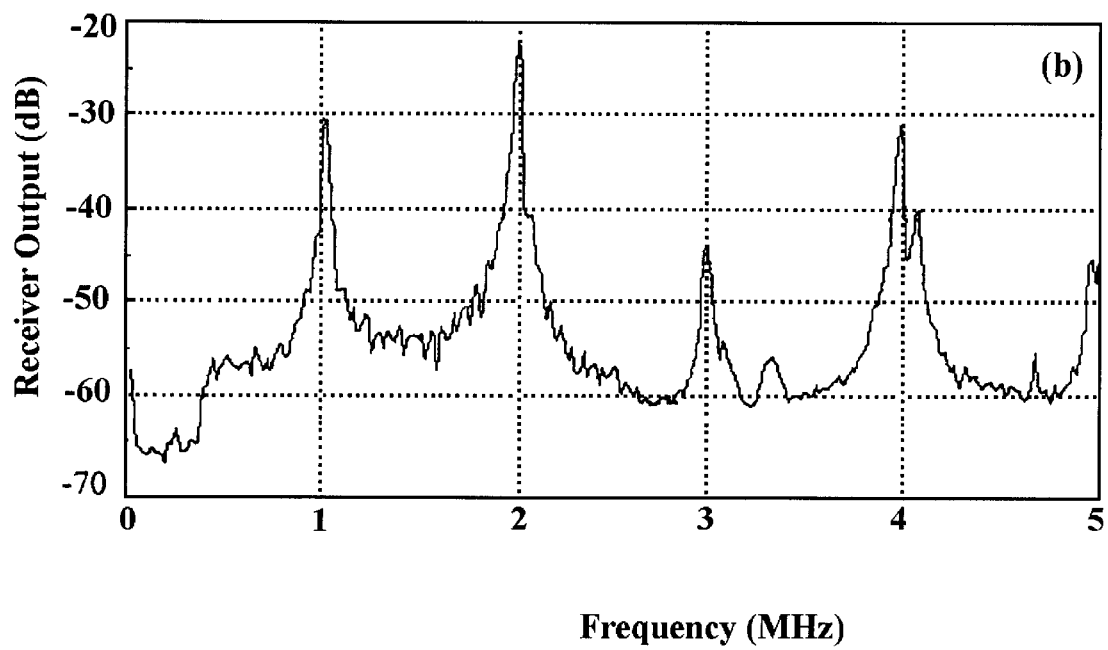
Figure 6C:
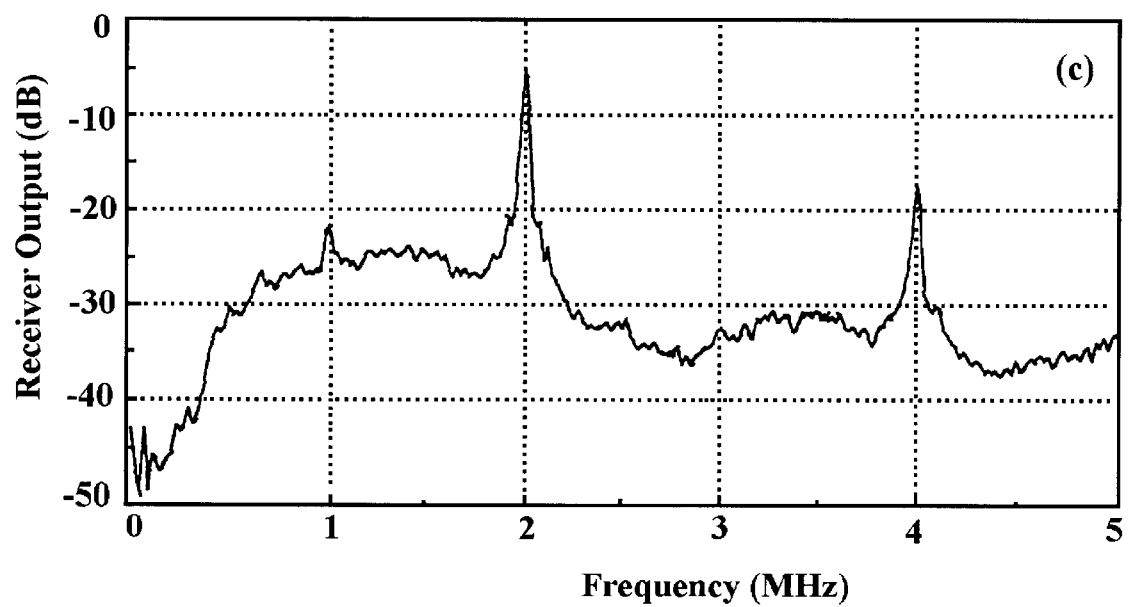

Subharmonic generation can be divided into three stages: occurrence, growth and saturation. In the occurrence stage (where the acoustic pressure is less than 0.3 MPa), the subharmonic component is insignificant. Such weak subharmonic response is demonstrated in the spectrum for an acoustic pressure of 0.23 MPa, as shown in FIG. 6(*a*). The peaks around 3.3 and 4.7 MHz are RF interference signals from air. This stage was not observed for the subharmonic response of free bubbles (Eller and Flynn. Generation of Subharmonics of Order One-Half by Bubble in a Sound Field. *J Acoust Soc Am* 46: 722–727, 1969; Neppiras, E. A. Subharmonic and Other Low-Frequency Emission from Bubbles in Sound-Irradiated Liquids. *J Acoust Soc Am* 46: 587–601, 1968). In the growth stage (where the acoustic pressure ranges 0.3–0.6 MPa), the subharmonic component grows with the acoustic pressure and usually has a high amplitude above the noise floor, as indicated in FIG. 6(*b*). The subharmonic signals at this stage may be utilized for subharmonic imaging and hydrostatic pressure estimation. As the acoustic pressure was increased, the growth of the subharmonic component became saturated. The noise floor was substantially raised due to bubble destruction (Shi, W. T., Forsberg, F. and Oung, H. Spectral Broadening in Conventional and Harmonic Doppler Measurements with Gaseous Contrast Agents. *Proc* 1997 *IEEE Ultrason Symp*, 1575–1578, 1997; Shi, W. T., Forsberg F, Everbach E C. Acoustic detection of microbubble destruction in gaseous contrast agents, *Proc* 16*th International Congress on Acoustics*, pp 2189–2190, 1998; Dayton, P. A., Morgan, K., Klibanov, A. L., Brandenburger, G. and Ferrara, K. W. Simultaneous Optical and Acoustical Observation of Contrast Agents, *Proc* 1997 *IEEE Ultrason Symp*, 1583–1591, 1997), as demonstrated in FIG. 6(*c*). In this stage, the signal-to-noise ratio of subharmonic signals was greatly reduced.

Figure 2:
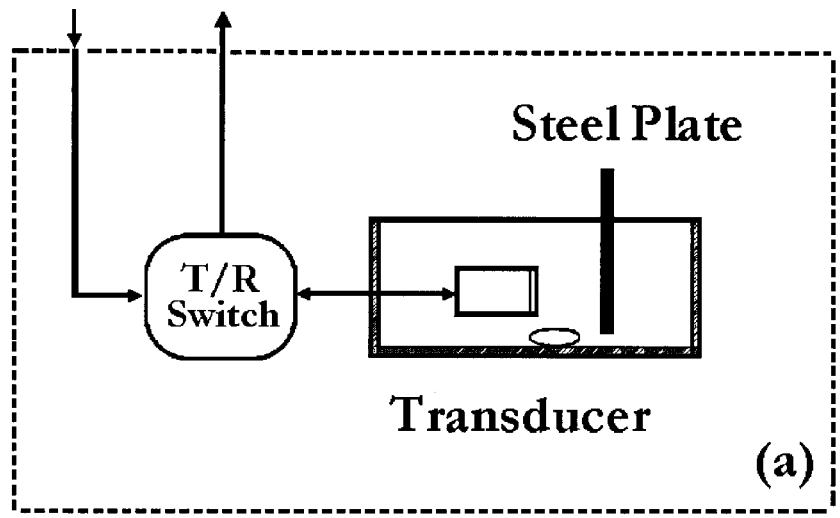
FIG. 2. Acoustic parts of the measurement system
Figure 2:
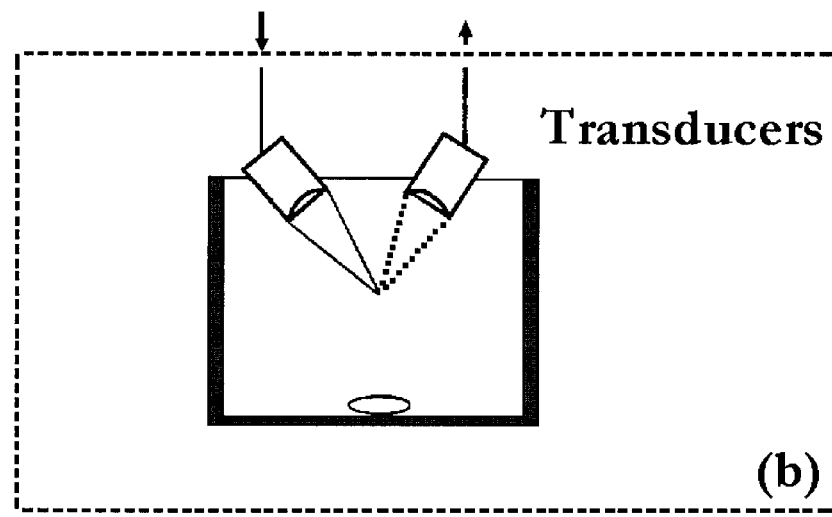
Figure 2:
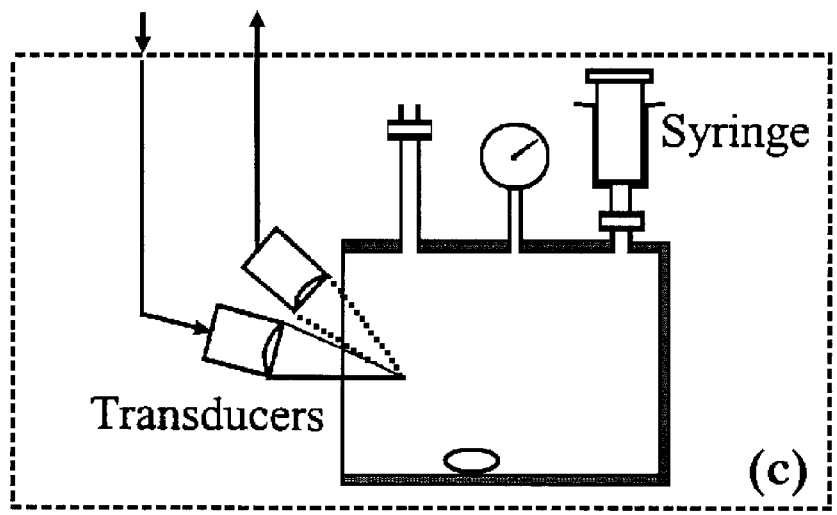
Figure 3:
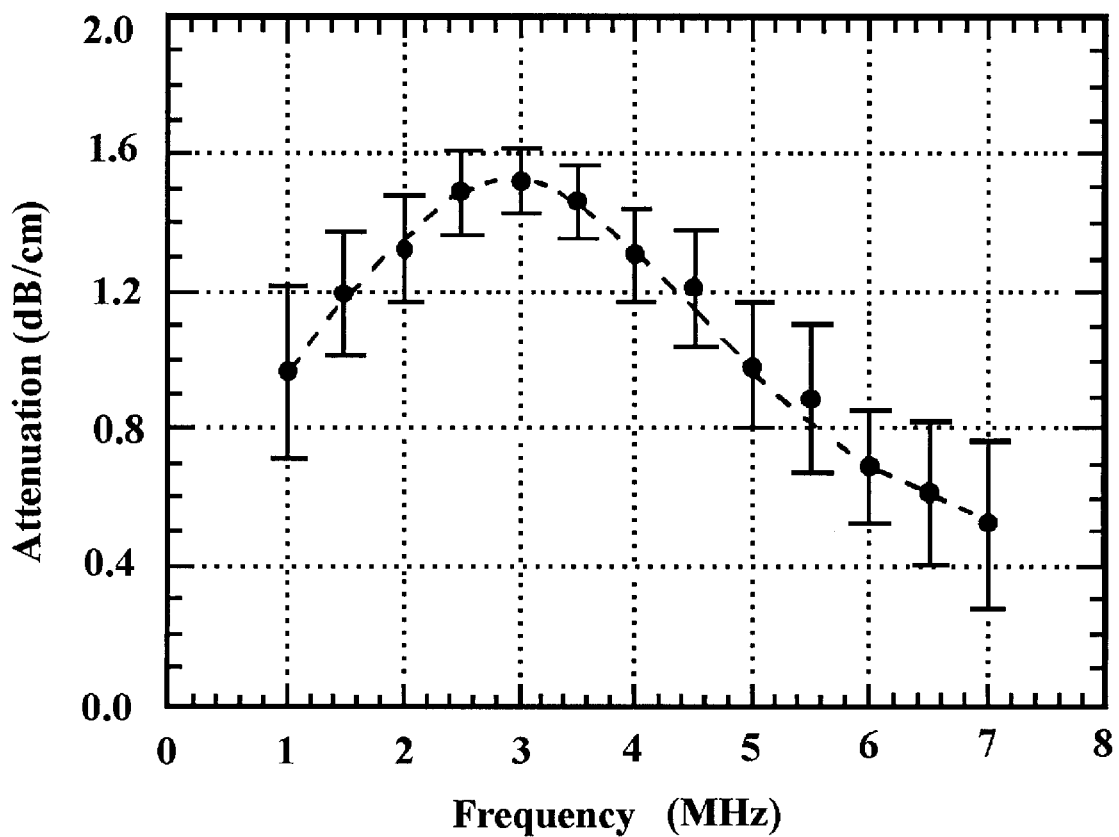
FIG. 3. Resonance response of Levovist

Subharmonic response of microbubbles at different hydrostatic pressures was investigated with the experimental setup shown in FIG. 2(*c*). The influence of the acoustic window on the subharmonic response at atmospheric pressure was initially tested by repeating the measurements described in the previous section. The experiments were carried out with an injection of 6.0 ml Levovist suspension into the 2.25 liter tank. The measured results were found to be very similar to the curve in FIG. 5. The acoustic penetration loss through the acoustic window on the tank wall was mostly compensated by the increase in acoustic output and the concentration of Levovist suspensions (raised to 0.56 gram/liter). By comparing the measurements in the seal tank with the data in FIG. 5, we were able to calibrate the transmit acoustic pressure inside the pressure tank.

Figure 7:
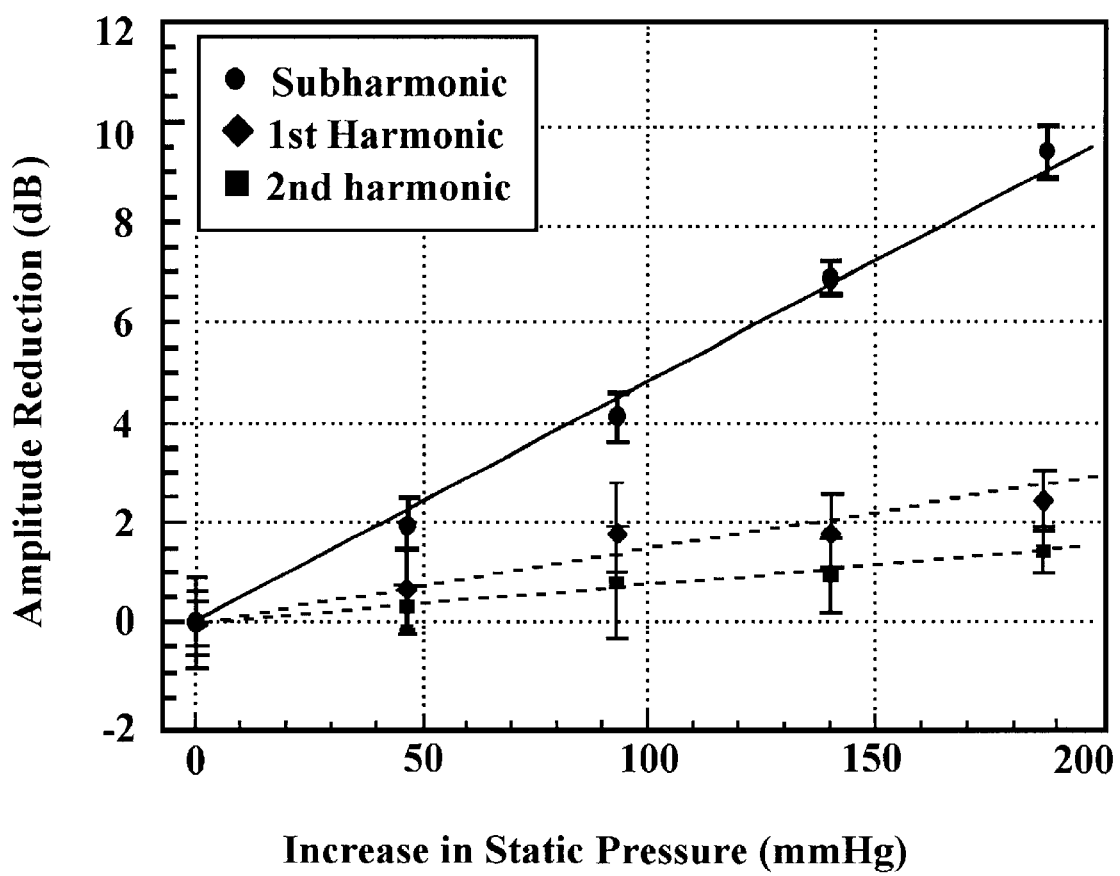
FIG. 7. Amplitude reduction versus over-pressure

The reductions in the first and second harmonic and subharmonic amplitudes at different over-pressures are demonstrated in FIG. 7 for a concentration of 0.56 gram/liter. During the experiments, the acoustic pressure amplitude was kept at 0.39 MPa. Over the over-pressure range of 0–186 mm Hg (which is the same as the range of human blood pressure variation), the first and second harmonic amplitudes decrease only 2.4 and 1.8 dB on average, respectively. This result is similar to the gray-scale measurements reported by Schlief (1997). On the other hand, over the same over-pressure range the subharmonic amplitude of scattered signals dropped by an average of 9.6 dB. An excellent correlation (r=0.98) between the subharmonic amplitude and static over-pressure was achieved. This correlation suggests that the dependence of the subharmonic amplitude on hydrostatic pressure can be employed for non-invasive pressure estimation.

The stability of Levovist in over-pressurized environment was tested with the following measurements: first, the average spectrum of 64 scattered signals was taken at atmospheric pressure; then, the microbubbles underwent a up-and-down pressurization, the average spectrum was again measured. During the up-and-down pressurization, the ambient pressure was raised to 200 mmHg and then reduced back to atmospheric pressure. The change in the amplitudes of subharmonic component in the spectra recorded before and after the up-and-down pressurization was found to be less than 0.8 dB. This means that Levovist can retain its strength of scattered signals after experiencing the up-and-down pressurization up to 0–200 mmHg. The stability of Levovist is probably due to the effect of the fatty acid on gaseous diffusion (Schlief, R. Galactose-based Echo-enhancing agents in *Ultrasound Contrast Agents*, edit by Barry B. Goldberg, Martin Dunitz Ltd, London. pp 75–82, 1997).

Figure 8:
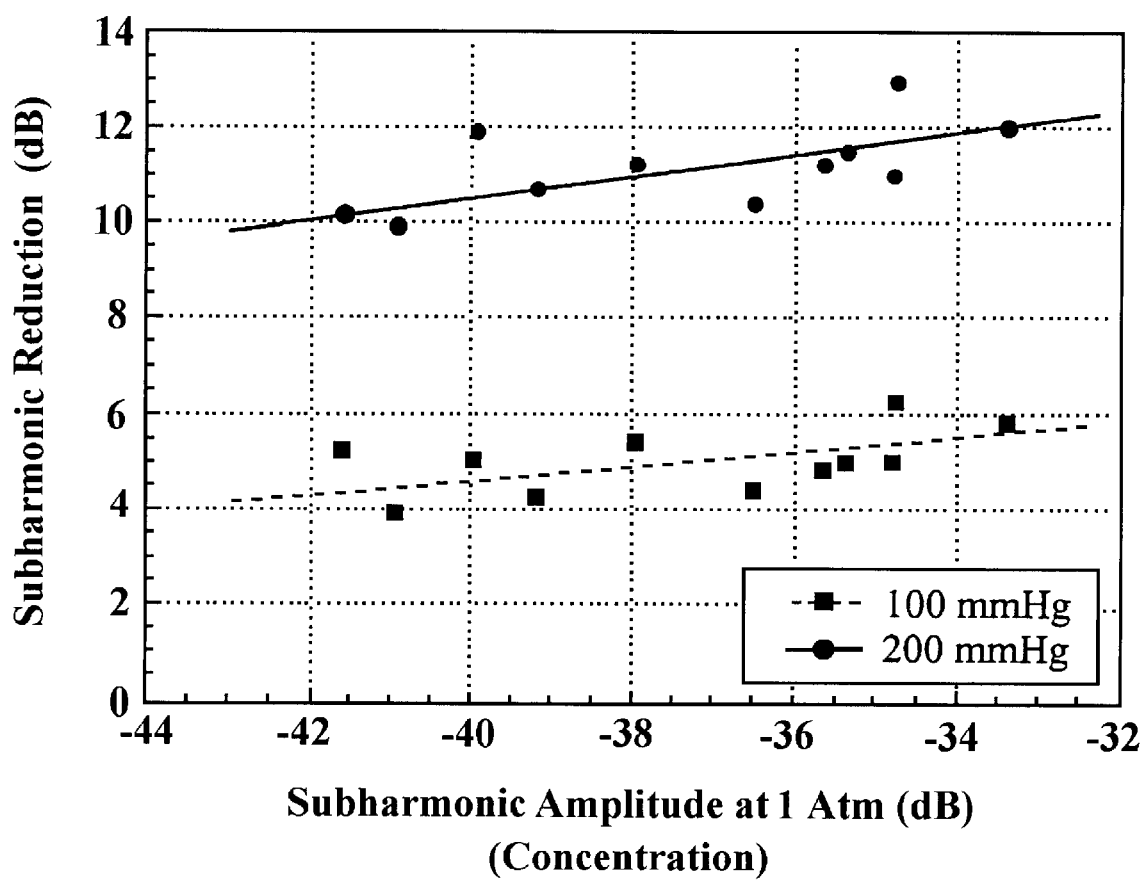
FIG. 8. Subharmonic reduction versus concentration

The influence of the microbubble concentration on subharmonic reduction was investigated with acoustic pressure amplitude kept at 0.39 MPa. FIG. 8 shows the subharmonic reduction at two constant over-pressures (100 and 200 mmHg) as a function of the received subharmonic signal amplitude at atmospheric pressure. The received signal amplitude is approximately proportional to the concentration of Levovist suspensions at lower concentrations. During a period of around 30 minutes, a total of 1 vial of Levovist suspension was injected. The concentration was increased from 0.56 to 2.0 gram/liter. The actual concentrations were lower than the administered concentration due to microbubble degeneration over time. The subharmonic reduction was shown to increase slightly as the received subharmonic signal amplitude at atmospheric pressure (which is correlated to the microbubble concentration) was more than tripled. This feature will be very important for pressure estimation because the subharmonic reduction in logarithm scale is almost independent of the absolute values of the received subharmonic amplitude.

Figure 9:
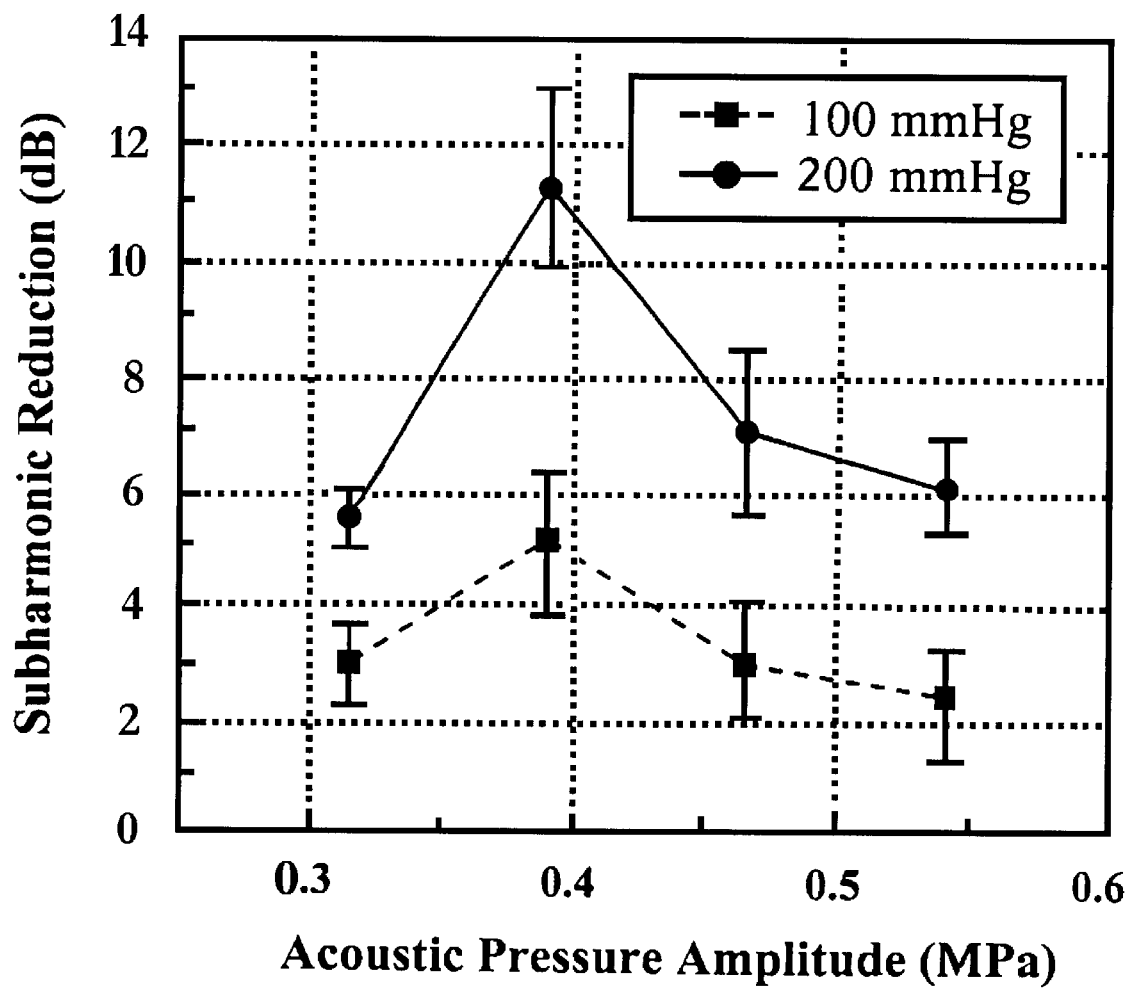
FIG. 9. Subharmonic reduction versus acoustic pressure

The reductions in the subharmonic amplitude due to the pressure increases of 100 and 200 mmHg as a function of acoustic pressure amplitude was given in FIG. 9. During the one-hour long measurement, a total of 2 vials of Levovist suspension was injected. The pressure-induced subharmonic reduction increased with the transmit ultrasound amplitude up to 0.39 MPa while the acoustic pressure amplitude covered the occurrence and growth stages of subharmonic generation. Afterwards the subharmonic reduction decreased due to the subharmonic saturation and the noise level elevation. Subharmonic reduction at the saturation stage became limited mainly because of the occurrence of microbubble destruction.

In summary, the subharmonic response to acoustic pulses of contrast microbubbles has been investigated. The subharmonic generation was found to undergo three stages: occurrence, growth and saturation. The significant subharmonic amplitude in the growth stage of the subharmonic generation can be used for both subharmonic imaging with optimal image contrast and non-invasive pressure estimation. Over the pressure range of 0–186 mm Hg, the subharmonic amplitude of scattered signals reduces by as much as 10 dB in the growth stage while the first and second harmonic amplitudes decrease less than 3 dB. This will allow the simultaneous performance of pressure estimation with subharmonic signals and imaging with the first and second harmonic signals using only one contrast agent.

An excellent correlation between the subharmonic component and hydrostatic pressure was obtained at the growth stage of subharmonic generation. This demonstrates the subharmonic component is a much better indicator of the hydrostatic pressure variation than the fundamental and second harmonic components. Based on above measurements, the present invention is a novel technique called SHAPE (Sub-Harmonic-Aided Pressure Estimation). By transmitting at one frequency but receiving only at its subharmonic frequency with digital or analog filtering techniques, SHAPE measures the hydrostatic pressure non-invasively according to a calibrated correlation curve of the hydrostatic pressure versus the subharmonic signal amplitude. It should be pointed out that scattered ultraharmonic signals (e.g., the order 3/2) can also be used in SHAPE (with receiving at the ultraharmonic frequency). This is because the behaviors of the ultraharmonics are very similar to those of the subharmonics (Llychev, V. I., Koretz, V. L. and Melnikov, N. P. Spectral Characteristics of Acoustic Cavitations. *Ultrasound* 27: 357–361, 1989; Shi, W. T. and Forsberg, F. Ultrasonic Characterization of the Nonlinear Properties of Contrast Microbubbles. (to be published) 1999). Since scattered subharmonic signals are much more sensitive to changes in the size of contrast microbubble than scattered first and second harmonic signals, SHAPE can further estimate the hydrostatic pressure by measuring shifts in the subharmonic (or ultraharmonic) resonance frequency of an agent containing uniform contrast microbubbles. A correlation curve between the subharmonic (or ultraharmonic) resonance frequency and the hydrostatic pressure can be obtained using the experimental system shown in FIG. 2(c). The subharmonic (or ultraharmonic) resonance frequency at a given hydrostatic pressure level can be determined by varying the transmit frequency to achieve the maximum amplitude of scattered subharmonic (or ultraharmonic) signals.

Figure 10:
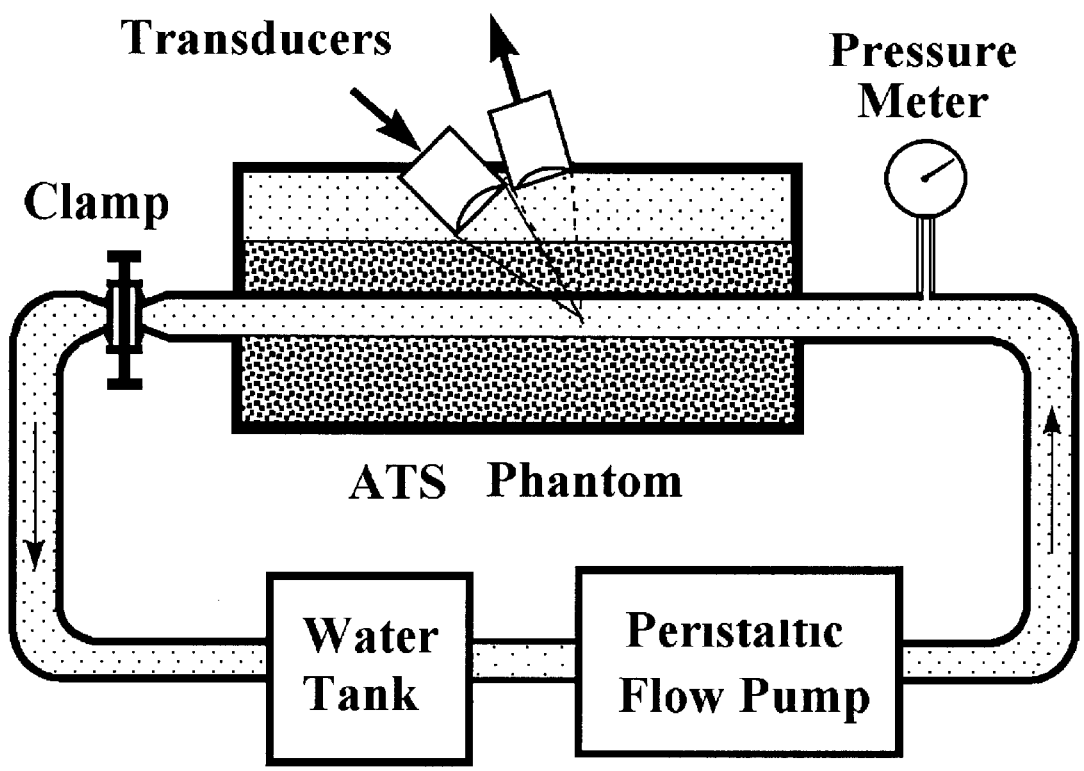
FIG. 10. A flow system for the test of SHAPE

SHAPE has been tested using a flow system shown in FIG. 10 as well as the electronic instruments given in FIG. 1. Two spherically focused transducers were employed for obtaining scattered signals from Levovist microbubbles inside a tissue-mimicking flow phantom (ATS Lab, Bridgeport, Conn.). One transducer (Staveley, East Hartford, Conn.) with a center frequency of 2.2 MHz and a bandwidth of 38% was used as the transmit transducer and another transducer (Etalon, Lebanon, Ind.) with a center frequency of 3.6 MHz and a bandwidth 86% was employed as the receiver. The transducers had the same diameter (1.2 cm) and a similar focal length (around 2.5 cm). The confocal region of the transducers was adjusted to be within an 8 mm vessel in the flow phantom. Water inside the vessel was kept in circulation by a peristaltic flow pump (Sarns, Ann Arbor, Mich.). The hydrostatic pressure inside the vessel was increased or decreased by tightening or releasing a clamp near the outlet of the phantom. The optimal acoustic pressure at the confocal region was obtained by achieving the maximum variation in the subharmonic amplitude as the hydrostatic pressure varied. All measurements were carried out with direct injections of contrast agents into a tank containing approximately one liter of water. The injected contrast agent was constantly mixed in the tank using a magnetic stirrer.

Figure 11:
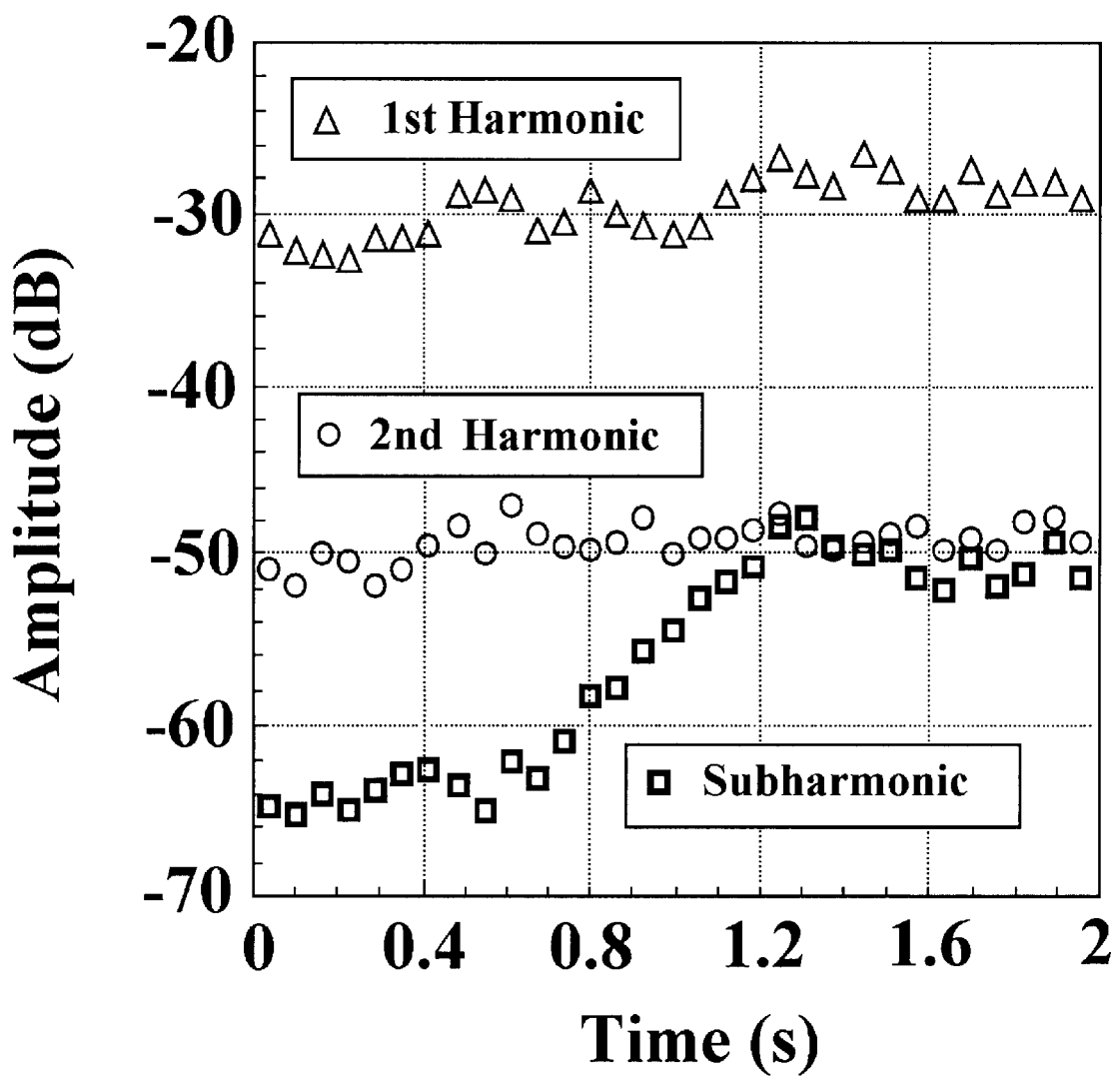
FIG. 11. The first and second and subharmonic amplitudes versus time

The amplitudes of the first and second harmonic and subharmonic components in 32 spectra (each averaged over 16 sequences) are recorded against time over a period of 2 seconds in FIG. 11. During the experiment, the hydrostatic pressure inside the vessel decreased as the clamp was released. Ultrasonic pulses with a center frequency of 2.0 MHz and a length of 32 cycles were transmitted at a PRF of 250 Hz. As shown in FIG. 11, the first and second harmonic amplitudes increase slightly as the hydrostatic pressure decreases. Over the same pressure range the subharmonic amplitude increases around 12 dB, which indicates a drop of about 200 mmHg in the hydrostatic pressure according the correlation between the subharmonic amplitude and the hydrostatic pressure. The predicted pressure drop (200 mmhg) has been confirmed by the reading of the pressure gauge.

The implementation of SHAPE will be carried out in both penetration and resolution modes. Excess dissipation resulting from the harmonic generation in tissue will be minimized in the penetration mode, while axial resolution will be maximized in the resolution mode using new filtering techniques such as the pulse-inversion method. Both mode can be applied to any body cavity in deep or shallow tissue structures. The pressure will be estimated according the correlation calibrated with the method given in FIG. 2(c) by measuring the amplitude of subharmonic signals.

In the penetration mode, relatively lower amplitude but longer transmit pulses (8 cycles or more) will be utilized. During the propagation of an intense acoustic wave, the waveform distorts and higher harmonics are generated (Muir, T. G. and Carstensen, E. L. Prediction of Nonlinear Acoustic Effects at Biomedical Frequencies and Intensities. *Ultrasound Med Biol* 6: 345–357, 1980). Acoustic energy initially at the transmit frequency will be transferred to the higher harmonics. Since ultrasound attenuation in tissue for higher frequency harmonics is much greater than that for the transmit acoustic wave, extra acoustic energy will be lost during the propagation from the source to the targeted imaging area. Such extra energy loss increase with both traveling distance and intensity of the ultrasound wave. Therefore, SHAPE in the penetration mode is especially suitable for estimating pressure inside deep cavities or vessels. Subharmonic signals in received echoes can be extracted with a low-pass filter (or a band-pass filter), because the narrow bandwidth of long transmit pulses enables the subharmonic to be separated from the first and higher harmonics in scattered signals. We have found that the subharmonic signal leaks at the beginning and end of long transmit tonebursts (Shi et al. Subharmonic Imaging with Gas-filled Microbubbles, *J Acoust Soc Am* 101, 3139 (abstract), 1997). Special care will be taken to reduce such transmit leakage by either tuning the transmit circuitry or adding a passive filter in the transmit circuitry.

In the resolution mode, relatively shorter transmit pulses (2–6 cycles) will be employed. The amplitude of the pulses must be great enough to maintain sufficient energy in each transmit pulse and, therefore, adequate signal-to-noise ratio for the received signals. Resolution can be as high as two cycles if 4-cycle pulses are transmitted. Subharmonic signals in the received echoes will be extracted using new filtering techniques such as (not limited to) the combination of a low-pass filter and the pulse-inversion technique. The low-pass filters will remove the second and higher harmonics in the received echoes and the pulse-inversion technique will cancel all the linearly scattered signals in the received echoes. This technique was previously employed by Chapman and Lazenby (1997) to enhance harmonic B-mode imaging. (Chapman, C. S. and Lazenby, J. C. (1997), Ultrasound Imaging System Employing Phase Inversion Subtraction to Enhance the Image. U.S. Pat. No. 5,632,277). It transmits a two-pulse sequence consisting of a short pulse, say $\eta_1(t)$, and the inverted copy of the first pulse $\eta_2(t)=-\eta_1(t-t_o)$ with a time delay $t_o$, respectively. By summing the scattered signals from these two transmit pulses, this technique will cancel out all linear scattering, that is, the first harmonic component in the combined scattered signal. But the cancellation can be achieved only if there is no relative motion between the transducer and the scatterer between the two pulses within the delay $t_o$. Therefore, SHAPE will suffer from a contrast reduction when they are used to detect fast moving structures in this mode.

Agents used in SHAPE will consist of gas-filled microbubbles including free microbubbles or microbubbles with thin coating or shell. The microbubbles must be flexible with good subharmonic response to ultrasound insonification. The microbubbles must be stable and capable of maintaining a stable size distribution in the measurement environment. Agents with narrow size distribution (or narrow resonance band) will be preferred for use in the penetration mode. The center frequency of transmit ultrasound pulses will be chosen near the peak subharmonic resonance frequency of such agents. The agents with wide band size distribution (or wide resonance band) will be preferred in the resolution mode. More microbubbles will be excited into resonance to enhance the signal-to-noise ratio of received signals. The agents with great growth slope will be best for the pressure estimation because such agents are capable of producing excellent correlation between the subharmonic signal and the hydrostatic pressure. The calibrated correlation will be used for the pressure estimation by measuring the amplitude of subharmonic signals. SHAPE can be implemented by designing a stand-alone system or modifying a commercial ultrasound scanner.

(a). Stand-alone systems.

The constant pressure or averaged pressure over time at a targeted location can be simply read out by a voltage meter, or the pressure variation as a function of time at a targeted location ca be displayed in a similar way as spectral Doppler.

Figure 12A:
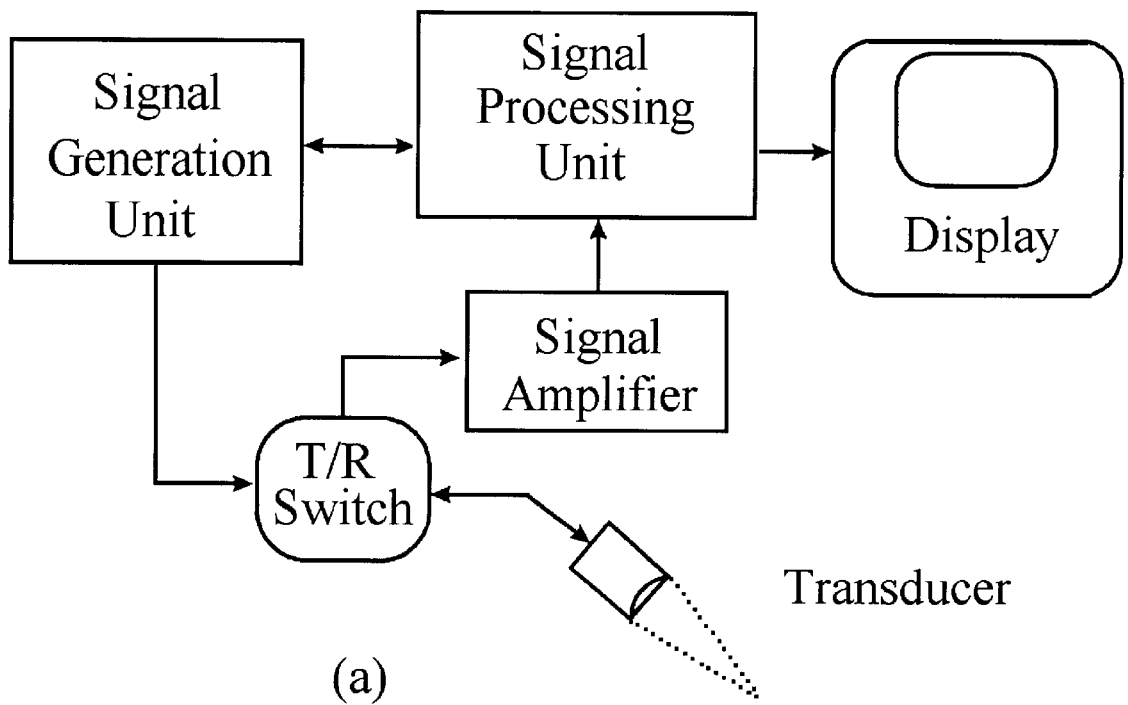
FIG. 12. Stand-alone systems
Figure 12B:
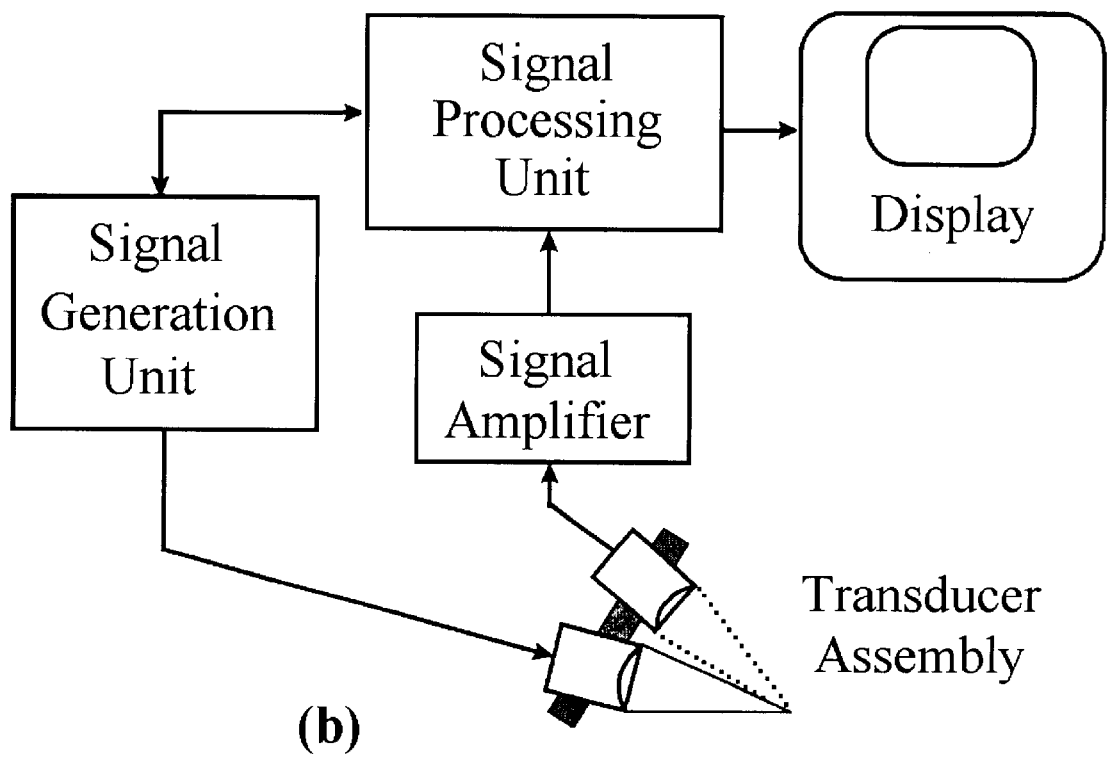

A single-element spherically focused transducer with a Transmit/Receiver switch can be used for general pressure estimation, as shown in FIG. 12(a). The spatial resolution will be determined by the transmit pulse length. Two single-element focused transducers in the confocal fixed setting can be used to maintain a fine spatial resolution of the pressure measurement when long transmit ultrasound pulses are required, as shown in FIG. 12(b). The spatial resolution will be determined by the size of the confocal region. The spatial resolution can be further improved using the subharmonic signals at $f_a-f_b/2$ (or $f_a+f_b/2$) with two incident ultrasound waves (center frequencies $f_a$ and $f_b$, where $f_b \leq f_a$), as shown in FIG. 12(c). The depth of the measurement is fixed with setup in FIGS. 12 (a), 12(b) and 12(c). In FIG. 12(a), the focused transducer may be replaced with a flat or less focused single-element transducer with a receive range gate for the measurement of pressure distributions simultaneously at different depths. The single-element transducers in FIGS. 12(a), 12(b) and 12(c) may also be replaced with annual, linear or curved transducer arrays for the pressure measurement at different depths.

(b). Modification of commercial ultrasound scanners

A commercial scanner can be modified for pressure measurement at certain locations or for the formation of 2-D pressure map. Pressure measurement at certain locations will be displayed as the pressure versus time in the similar way as spectral Doppler. The 2-D pressure map will be displayed in similar way as color Doppler.

The pressure measurement and mapping can be performed with a phase-array with capability of beam steering, or with a linear array, or with a curved array. The array will be used in pulse-echo mode to detect the backscattered subharmonic signals from contrast microbubbles at a certain depth. The sample size in pressure measurement will be controlled with a variable range gate as employed in spectral Doppler. The axial resolution in 2-D pressure map will be determined by the length of the transmit pulse.

The pressure measurement particular with a linear or curved array can be performed with two beams formed on each side of the array to simulate two single-element focused transducer. The two beams are steered to form a confocal region where the pressure estimation will be made. This design will be very useful when long transmit ultrasound pulse are required. The spatial resolution will be determined by the dimension of the confocal region.

Both the pressure measurement and 2-D mapping can be carried out simultaneously with conventional or harmonic imaging. For some contrast agents, the subharmonic response is very sensible to pressure change while the first and second harmonics are insensible to pressure changes (e.g., for Levovist, around 10 dB subharmonic reduction and 2 dB second harmonic reduction over 0–186 mmHg). Color-coded pressure map can be overlapped on the conventional and harmonic gray-scale images. M-mode pressure measurement can also be conducted. That is, firing subsequent A-lines along one line of sight and estimate the pressure at each depth before displaying the information as a function of depth and time in a similar way as M-mode.

We claim:

1. A method of measuring pressure in a mammal, comprising:

administration of a diagnostically effective amount of a contrast agent containing microbubbles into said mammal;

applying an ultrasound system said ultrasound system transmitting at least one ultrasound detection signal and receiving ultrasound signals scattered by said microbubbles, said ultrasound system being equipped with analog or digital filters extracting subharmonic signals of the ½ order (at half the transmit frequency) from said scattered signals from said microbubbles; and measuring subharmonic signal amplitude to estimate said pressure in said mammal according to a calibrated correlation curve of hydrostatic pressure versus the subharmonic signal amplitude.

2. A system for measuring pressure in a mammal, comprising:

an ultrasound system with analog or digital filtering for detecting microbubbles, said ultrasound system capable of transmitting at least one detection signal and capable of receiving detection signals that are scattered and returned by said microbubbles, wherein said detection signals received by said ultrasound system include at least one of the group of subharmonic and ultraharmonic signals of the ½ order (at half the transmit frequency) from said scattered signals from said microbubbles;

said ultrasound system having at least one single-element transducer for pressure estimation according to a calibrated correlation curve of hydrostatic pressure versus the subharmonic signal amplitude.

3. A system for measuring pressure in a mammal, comprising:

an ultrasound system with analog or digital filtering for imaging microbubbles, said ultrasound system capable of transmitting at least one detection signal and capable of receiving detection signals that are scattered and returned by said microbubbles, wherein said detection signals received by said ultrasound system include at least one of the group of subharmonic and ultraharmonic signals of the ½ order (at half the transmit frequency) from said scattered signals from said microbubbles;

said ultrasound system having one of the group of a phase transducer array with a capability of beam steering, a linear transducer array with at least one transducer, or a curved transducer array to measure subharmonic signal amplitude to estimate said pressure in said mammal according to a calibrated correlation curve of hydrostatic pressure versus the subharmonic signal amplitude.

4. An ultrasound contrast agent used for pressure estimation with said ultrasound contrast agent containing microbubbles, comprising an ultrasound contrast agent having microbubbles with a narrow band of size distribution and stability when circulating in vivo within a mammal bloodstream such that size uniformity of said microbubbles is maintained during circulation and said microbubbles are substantially compressible such that said microbubbles change significantly in size in response to changes in pressure and said response of said microbubbles to changes in pressure maximizes the intensity of at least one of the group of subharmonic and ultraharmonic signals of the ½ order (at half the transmit frequency) scattered from said microbubbles.

5. A method of using an ultrasound contrast agent containing microbubbles to estimate pressure in a mammal, comprising:

administration of said microbubbles to said mammal in vivo, wherein said microbubbles have a narrow band of size distribution and are substantially compressible such that said microbubbles change significantly in size in response to changes in pressure;

application of an ultrasound system to said contrast agent, said ultrasound system transmitting at least one ultrasound detection signal and receiving ultrasound signals scattered by said microbubbles and said ultrasound system extracting signals of the ½ order (at half the transmit frequency) from said scattered signals from said microbubbles; and measurement of shifts in resonance frequency of one of the group of subharmonic or ultraharmonic signals received by said ultrasound system having analog or digital filtering for detection of said microbubbles, wherein said resonance frequency shifts result from changes in the size of said microbubbles and said size changes correspond to changes in hydrostatic pressure in said mammal.

* * * * *